United States Patent [19]

Bremer et al.

[11] Patent Number: 4,838,264

[45] Date of Patent: Jun. 13, 1989

[54] TORQUE LIMITING DEVICE FOR USE WITH BONE PENETRATING PINS

[75] Inventors: Paul W. Bremer, Jacksonville, Fla.; David A. Kesselman, Sonoma, Calif.

[73] Assignee: Bremer Orthopedics, Inc., Jacksonville, Fla.

[21] Appl. No.: 86,709

[22] Filed: Aug. 18, 1987

[51] Int. Cl.⁴ .............................................. A61B 17/00
[52] U.S. Cl. .................................. 128/303 B; 128/75; 411/2
[58] Field of Search ...................... 128/75, 84 R, 87 R, 128/303 B; 411/386, 1, 2; 81/120, 121.1, 177.1, 124.5, 461, 467, 471

[56] References Cited

U.S. PATENT DOCUMENTS

| | | | |
|---|---|---|---|
| 1,398,842 | 11/1921 | Cruse | 128/303 B |
| 2,740,315 | 4/1956 | Gouverneur, II | 81/471 |
| 3,072,118 | 1/1963 | Standerwick et al. | 128/87 R |
| 3,331,267 | 7/1967 | Tietge | 81/471 |
| 3,391,693 | 7/1968 | Georgiade et al. | 128/87 R |
| 3,604,412 | 9/1971 | Gardner | 128/75 |
| 3,669,102 | 6/1972 | Harris | 128/84 R |
| 3,923,046 | 12/1975 | Heifetz | 128/75 |
| 4,251,600 | 8/1980 | Wesselman | 81/471 |
| 4,612,930 | 9/1986 | Bremer | 128/303 B |
| 4,667,660 | 5/1987 | Eingorn | 128/75 |

FOREIGN PATENT DOCUMENTS

| | | | |
|---|---|---|---|
| 3538593 | 5/1987 | Fed. Rep. of Germany | 128/92 YZ |
| 2486852 | 7/1980 | France | 81/471 |
| 854792 | 11/1960 | United Kingdom | 81/471 |

OTHER PUBLICATIONS

"Guard-Nut" ® Brochure, May, 1980.

*Primary Examiner*—Richard J. Johnson
*Assistant Examiner*—Cahrles H. Sam
*Attorney, Agent, or Firm*—Nixon & Vanderhye

[57] ABSTRACT

A bone penetrating pin for medical use includes, in one embodiment, a shank provided at one end with a bone penetrating element of titanium or single crystal alumina ceramic material, and a driving head at the other end. A removable cap is applied to the driving end, the cap including upper and lower cylindrical portions of substantially identical diameters interconnected by an intermediate portion of substantially smaller diameter. The upper portion is formed with oppositely extending arms for application of torque through the cap to the shank and bone penetrating element. The intermediate portion of the cap is designed to fail in shear upon the application of torque in excess of a predetermined maximum; that is, it provides a torque limiting function. In another embodiment, the torque applying and limiting means are in the form of a tool assembly comprising a shank engageable with one end of a bone penetrating pin, and a cap slidable with respect to the shank, wherein a torque limiting insert is receivable between the cap and the shank to drivingly couple the two. More specifically, the tool of this second embodiment includes an elongated shank provided with a pin fastener engaging tip at one end and a first socket formed at the other end. A torque applying device is slidably mounted with respect to the shank, and includes a second socket substanially aligned with the first socket. A torque limiting insert is receivable within the first and second sockets to couple the torque applying device and the pin engaging shank.

30 Claims, 3 Drawing Sheets

TORQUE LIMITING DEVICE FOR USE WITH BONE PENETRATING PINS

BACKGROUND AND SUMMARY OF THE INVENTION

This invention relates to bone penetrating pins and associated devices for applying and limiting torque during the installation thereof. Such pins are used in various medical procedures, including, but not limited to those relating to the cervical spine and skull. For instance, a patient's head must be held in a fixed, predetermined position while a fracture or dislocation of the cervical spine is healing, by utilizing a conventional halo traction device or, during neurosurgery, utilizing an operating table head holder. While the patient's head is being immobilized, it may also be desirable to subject the patient's skull to an imaging procedure, such as a CT scan, digital subtraction angiography, sonography, magnetic resonance imaging, computer enhanced flat film X-raying, and the like. Therefore it is highly desirable that the affixation apparatus be made of a material which does not artifact significantly, i.e., to any greater extent than bone matter.

It is also desirable during a number of other surgical procedures to quickly and accurately insert fastener pins in bone material.

It is also desirable, during such procedures, to be able to install such pins without utilization of complex, specialized, and consequently expensive tooling and the like.

In applicant's prior U.S. Pat. No. 4,612,930, skull pins, which are constructed in such a way that they do not artifact significantly, and related crown apparatus are disclosed which avoid any interference with imaging, but which nevertheless provide effective skull fixation. The subject matter of this earlier patent is incorporated herein by reference.

According to this invention, torque applying and torque limiting devices are disclosed which enable quick, precise and accurate installation of bone penetrating pins.

In one embodiment of the invention, the torque applying and limiting functions are embodied in a cap which may be detachably mounted with respect to the pin itself.

In this first embodiment, the pin includes a bone engaging portion which terminates in a pointed tip, and which is composed of a first material, such as ceramic or titanium. Most desirably the bone engaging portion is of a single crystal ceramic material, such as single crystal alumina ceramic, commercially sold under the trademark "BIOCERAM" of Kyocera International, Inc. of West Lost Angeles, Calif. This material does not artifact any more than bone matter; however, it has a brittleness which mitigates against formation of the entire pin of the material. Therefore, the bone penetrating pin according to the invention also comprises an exteriorly threaded, elongated cylinder or shank, of a second material that is radiolucent, such as plastic or aluminum. Preferably, the second material is a plastic. The bone engaging portion is fixed to the plastic or aluminum cylinder in any suitable manner. For example, the bone engaging portion may be formed with a rearwardly extending shaft received within an opening provided in an end face of the elongated cylinder. If the cylinder is plastic, it may be molded about the shaft extension of the bone penetrating portion. If the cylinder is metal, the shaft extension may be secured within the cylinder by epoxy adhesive or the like. The cylinder is provided at its opposite end with a blunt, driving end, and preferably having a screwdriver blade-receiving slot formed therein.

In accordance with this first embodiment of the invention, a removable plastic cap is utilized, which fits over the blunt driving end of the pin, and which is designed for performing the dual function of applying the torque necessary to install the pin, and of preventing an over-torqued situation by failing upon the application of torque greater than a predetermined maximum.

The removable cap is formed as a single element, comprised of upper and lower cylindrical portions separated by an intermediate, cylindrical portion of smaller diameter than the upper and lower portions. Torque applying means, in the form of outwardly extending "wings" or "arms" are integrally formed within the upper portions of the cap. The lower portion of the cap is provided in its lower end face with a bore having a peripheral shape complimentary to the shape of the blunt, driving end of the cylinder. In a preferred embodiment, the blunt driving end and lower cap bore have substantially square shapes, although other shapes, e.g., hexagonal, may also be employed.

It will be understood that torque applied at the upper portion of the cap is transmitted to the lower portion via the intermediate portion. This intermediate cylindrical portion of smaller diameter is designed to fail upon the application of torque exceeding a predetermined maximum level. When the maximum level is exceeded, the upper portion of the cap shears off at the intermediate portion, and is rendered inoperable for torque applying purposes. In such case, when it is desired to remove the pin, a screwdriver or similar tool may be utilized in conjunction with the slot in the upper end face of the cylindrical shank, which is exposed upon removal of the upper portion of the cap.

In a further aspect of the invention, the penetrating pins are utilized as skull pins in conjunction with a halo crown of the type described in my previously mentioned prior patent.

In another embodiment of the invention, the torque applying and limiting means are in the form of a tool assembly comprising a shank engageable with one end of a bone penetrating pin and a cap slidably mounted with respect to the shank, wherein a torque limiting insert is receivable between the cap and the shank to drivingly couple the two. More specifically, the tool of this second embodiment includes an elongated shank provided with a pin fastener engaging tip at one end and a first socket formed at the other end. A torque applying device is slidably mounted with respect to the shank, and includes a second socket substantially aligned with the first socket. A torque limiting insert is receivable within the first and second sockets to couple the torque applying device and the pin engaging shank.

The torque limiting insert is provided with an upper portion having a cross-sectional shape complimentary to that of the second socket; and a lower portion having a cross-sectional shape complimentary to the first socket. The upper and lower portions of the insert are interconnected by an intermediate, grooved area which is designed to fail in shear upon the application of torque beyond a predetermined maximum.

Other objects and advantages of the invention will become apparent from the detailed description of the invention which follows hereinbelow.

DETAILED DESCRIPTION OF THE INVENTION

Figure 1:
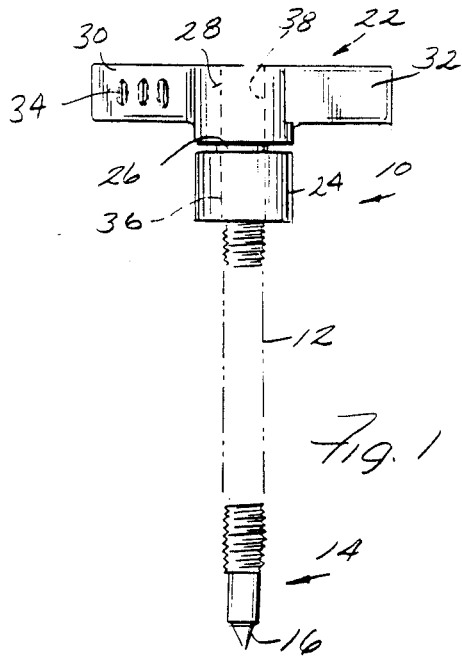
FIG. 1 is a front view of an exemplary bone penetrating pin according to the present invention.

Referring to FIGS. 1-6, an exemplary bone penetrating pin 10 in accordance with the present invention is illustrated in detail. The pin includes an elongated cylinder or shank 12 which terminates at a first bone penetrating end 14 including a pointed tip 16. The bone penetrating portion 14 is preferably constructed of titanium or a ceramic material, and most preferably a single crystal ceramic material such as "BIOCERAM". This material is ideally suited for bone penetration, yet it does not artifact anymore than does bone material. It is, however, somewhat brittle and, therefore, it is necessary to form the cylinder 12 of a different material than the bone penetrating portion 14. For example, the cylinder may be made of aluminum or a plastic material such as carbon fiber or boron fiber reinforced plastic that has sufficient rigidity and strength to be utilized in bone penetrating pin construction. The cylinder or shank is illustrated as having a series of threads thereon so that the pin may be utilized with an associated force reaction device, such as a halo crown, provided with threaded apertures through which the pins are threadably received.

The bone penetrating portion 14 is rigidly connected to the cylinder 12 by any suitable means. For example, the bone penetrating portion 14 may include a stub shaft (not shown) received within a bore formed in the lower end of the threaded cylinder 12, and secured therein by epoxy adhesive or the like. Alternatively, in the event threaded cylinder 12 is a plastic material, the threaded cylinder may be molded and solidified around the stub shaft during the formation of the cylinder.

The other end of the threaded cylinder 12 terminates in a blunt driving head 18, preferably integrally formed with the cylinder. The blunt driving head 18 is formed with a polygonal peripheral shape, preferably square, or hexagonal, etc. and across which a screw driver receiving slot 20 is formed.

Figure 2:
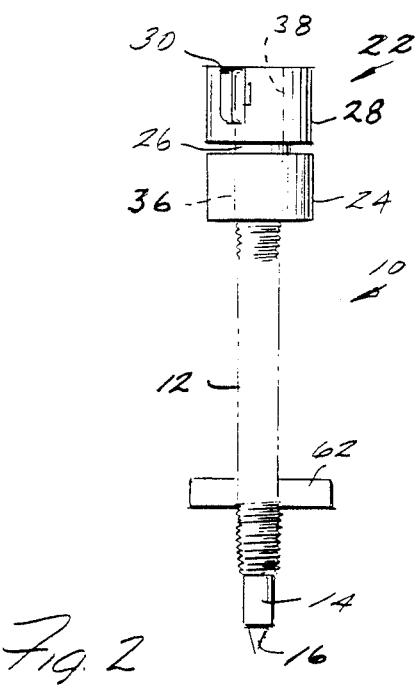
FIG. 2 is a side view of the pin of FIG. 1, and showing a locking nut in association therewith.
Figure 3:
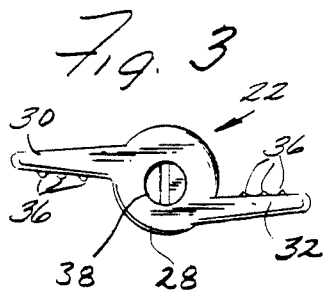
FIG. 3 is a top view of the pin illustrated in FIG. 1.
Figure 4:
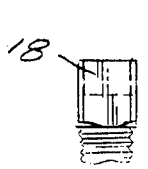
FIG. 4 is a partial side view of the pin shown in FIG. 1 but with the cap removed.
Figure 5:
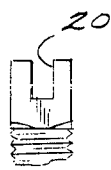
FIG. 5 is a partial end view of the pin shown in FIG. 4.

The bone penetrating pin also includes a removable torque applying and torque limiting cap 22, preferably of one-piece molded plastic construction, and designed to be received over the blunt driving head 18 in the manner described hereinbelow. The cap is formed with a lower cylindrical portion 24, an intermediate cylindrical section 26 and a upper cylindrical section 28. As best seen in FIGS. 1 and 2, the intermediate section 26 has a significantly smaller diameter than either of the upper and lower portions 24 and 28. Upper portion 28 is further formed with a pair of outwardly extending torque applying arms 30, 32 which permit the cap 22 to be turned in the manner of a conventional wing nut. Opposite side surfaces of the arms 32, 34 are formed with projecting ribs 34 to facilitate firm gripping of the cap without slippage.

Figure 6:
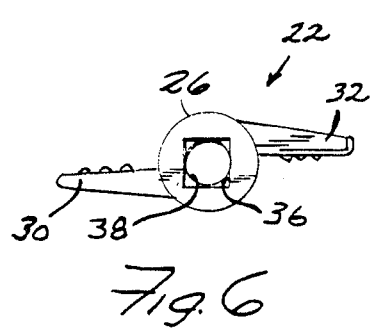
FIG. 6 is a bottom view of the removable cap.

The lowermost end face of the removable cap 22 is formed with an opening 36, the peripheral shape of which is shown to be square, corresponding to the peripheral shape of the blunt driving head 18. The opening 36 extends axially through substantially the entire lower portion of the cap, terminating just short of the intermediate portion 26. A cylindrical bore 38 extends from the termination of square opening 36, and through the intermediate and upper portions 26, 28, respectively. Because the square opening extends to the interface with intermediate portion 26, torque forces are transmitted to the shank immediately adjacent the smaller intermediate portion of the cap. It will be understood, as best seen in FIG. 6, that the removable cap 22 may be inserted over the driving head 18 much in the same manner as a bolt head and socket wrench connection.

The smaller diameter intermediate portion 28 of the cap 22 serves as a torque limiting device which is designed to fail upon the application of torque in excess of a predetermined maximum. Specifically, failure in shear occurs so that the upper portion 28 of the cap 22 is separated from the lower portion 24. It will thus be understood that the bone penetrating pin may be quickly and accurately installed without danger of overtightening, and that precise torque control is achieved by reason of the cap construction described hereinabove.

Figure 7:
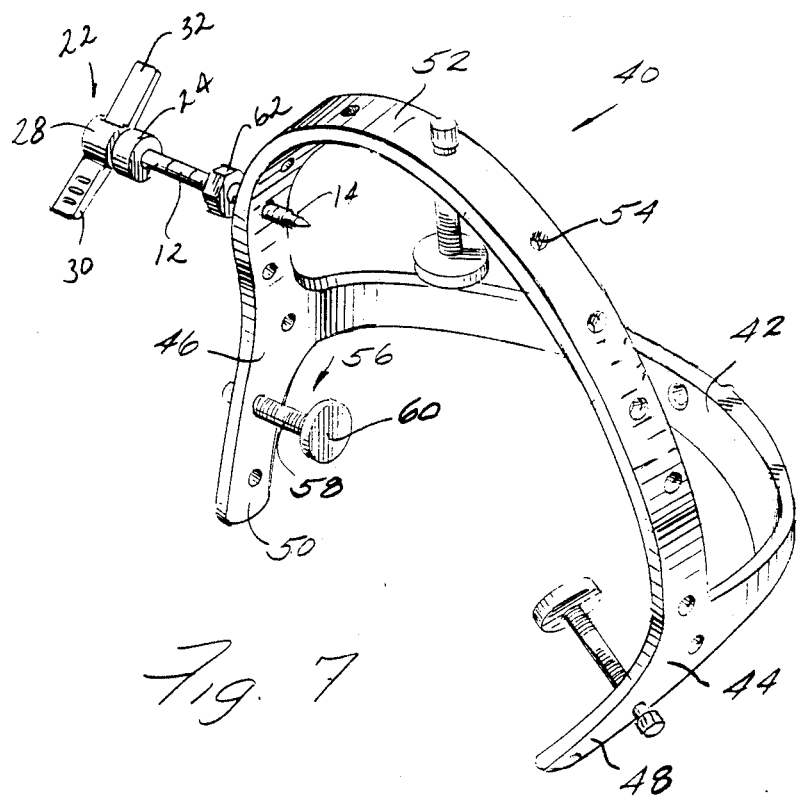
FIG. 7 is a a perspective view of a halo crown designed for use with the subject invention.

Turning now to FIG. 7, there is disclosed a device for holding a patient's head in a predetermined stationary position during a medical treatment or operative procedure. The apparatus, similar to that shown in my prior U.S. Pat. No. 4,612,930, comprises a generally ring-shaped member 42 which is rigid and preferably constructed of a material that does not artifact significantly so that it does not cause blockage during CT scanning, magnetic resonance imaging, or the like. The ring-shaped member 42 terminates at ends 44, 46 which slant at an angle with respect to the remainder of the ring, so that at least a portion of the crown lies below the "equator" of the patient's head during use. The apparatus also includes a reinforcing portion 52 which is adapted to extend over the patient's head and connect side portion 44 with side portion 46. A plurality of threaded apertures 54 are formed in the reinforcing portion as well as in the crown portion. These apertures are designed to receive a plurality, preferably three, positioning devices 56, each of which includes a threaded stem 58 and a positioning pad 60. Three or four positioning pads are effective to hold the crown in place while the skull pins are applied.

The bone penetrating pins previously described with reference to FIGS. 1-6 may be employed as skull pins in the apparatus illustrated in FIG. 7. In addition, the skull pins may each be equipped with a lock nut 62 to prevent loosening and to stabilize the pins from wobbling in the threaded holes of the crown. A lock nut of this type is illustrated in both FIGS. 2 and 7.

In the event that torque beyond the predetermined maximum is supplied to the skull pins, the removable cap will shear in the intermediate area 28, providing a clear indication that maximum torque has been applied, and making it impossible to further tighten the pins. The pins may thereafter be removed at the completion of the medical procedure, by a conventional screwdriver engageable in the the slot 20 formed in the blunt driving head 18.

Figure 8:
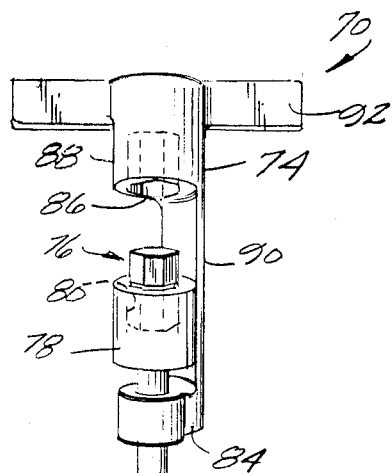
FIG. 8 is a side view of an alternative embodiment of the invention.
Figure 8:
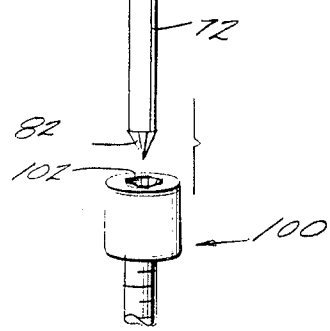
Figure 9:
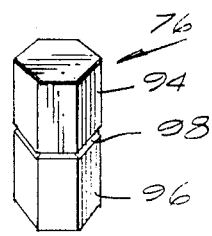
FIG. 9 is a detailed view of a torque limiting insert included in the device illustrated in FIG. 8.

Turning now to FIGS. 8 and 9, a torque limiting tool for use in the installation of bone fasteners during surgery is disclosed which incorporates the torque limiting concept of the invention.

The tool 70 includes generally an elongated shank portion 72, a torque applying handle 74 and a torque limiting device 76. The shank 72 is preferably formed of metal, while the entire torque applying handle 74 may be investment cast stainless steel or injection molded plastic.

The elongated shank 72 includes an enlarged head 78 at one end, and a working tip 82 at the other end. The enlarged head 78 is formed with an internal socket 80 for a purpose to be described in greater detail hereinbelow. The torque applying handle 74 includes a lower retention sleeve 84 which maintains the torque applying handle in a slidably captured relationship with the shank 72, and a socket 86 formed in an upper portion 88 to which a torque applying T-handle or knob 92 is secured. Sleeve 84 and socket 86 are connected by an integrally formed, intermediate portion 90.

It will be understood that the socket 80 in the enlarged end 78 of the shank 72 is substantially vertically aligned with the socket 86 formed in the upper portion 88 of the torque applying handle 74.

A torque limiter 76 is provided, one end of which is adapted to be received in the socket 80, and the other end of which is adapted to be received in the socket 86. The torque limiter 76 includes an upper generally hexagonal portion 94 and a similar lower portion 96, interconnected by a torque limiting groove 98 formed approximately midway along its length.

The torque limiting device 76 is preferably formed of a plastic material and the depth of groove 98 may be cut as required, to fail upon application of a selected maximum torque. It will be appreciated that the torque limiting device 76 may be formed to fail at any number of desired maximum torque levels. In order to faciliate proper selection of torque limiters for any particular application, the torque limiting elements may be coded, as by coloring or other suitable means, to indicate the various failure levels.

In operation, an appropriate torque limiting element will be selected, and its lower end 96 will be inserted into the socket 80 of the shank 72, as shown in FIG. 8. The torque applying handle 74, including socket 86, intermediate portion 90 and sleeve 84 will then be moved downwardly along the shank 72 until the socket 86 engages and receives the upper portion of the torque limiting element 94. Thereafter, the tool may be used in association with a pin-type bone fastener as illustrated in schematic form at 100 in FIG. 8. The bone fastener typically will include a driving head including a tool engaging slot 102 which may be of any conventional configuration such as a regular screwdriver slot, a Phillips head screwdriver slot, a hexagonal slot, etc. It will be understood that the tip portion 82 of the shank 72 will be similarly configured for application of torque to the fastener 98. It will be further understood that the shank 72 may be designed to receive interchangeable tips of various configurations, as determined by the slot design employed on the driving head of the fastener.

During the application of torque to the bone fastener 98, if and when a predetermined maximum level is exceeded, the hexagonal torque limiting element 76 will fail in shear at the groove 98 between upper portion 94 and lower portion 96 of the torque limiting element 76. In this manner, the torque limiting tool is reusable indefinitely merely by insertion of a new torque limiting element which may be of the same or different torque failure level. At the same time, once the limiter 76 fails, the surgeon knows the pin is torqued as required and that it is time to move on to the installation of the next pin upon replacement of the failed torque limiter.

In an alternative embodiment, the intermediate connecting portion 90 extending between socket 86 and sleeve 84 may have a tubular configuration, enclosing the enlarged shank head 78, and merging with sleeve 84. In such case, it will be appreciated that socket 86 may then be extended through the upper portion 88 of the torque applying handle 74. To insert a torque limiter element 76, one merely slides the element into socket 86 through the top of the handle 74, with perhaps some rotational adjustment to align the lower socket 80 with upper socket 86 to insure correct placement of the limiter 76 in the lower socket 80.

It will be understood that while the bone penetrating pins of this invention have been disclosed in one particular embodiment for use with skull stabilizing apparatus, the pins have applicability in any bone penetrating application as will be understood by those skilled in the art. It will thus be seen that according to the present invention, a simple yet effective apparatus has been disclosed which enables installation of a bone penetrating pin without specialized tooling, but which assures proper and accurate installation by limiting the torque which may be applied to the pin.

While the invention has been herein shown and described in what is presently conceived to be the most practical and preferred embodiment thereof, it will be apparent those of ordinary skill in the art that many modifications may be made thereof within the scope of the invention, which scope is to be accorded the broadest interpretation of the appended claims so as to encompass all equivalent structures and procedures.

I claim:

1. In combination with a bone penetrating pin, a device for anchoring said pin in bone material comprising separable cap means adapted for engagement with an elongated shank, said cap means including torque applying means and means for transferring torque to said elongated shank; said means for transferring torque to said elongated shaft including torque limiting means designed to fail upon application of torque exceeding a predetermined maximum, said pin further including means for facilitating removal of said pin from the bone whether or not said torque limiting means has failed.

2. The combination as defined in claim 1, wherein said elongated shank is integrally formed with said bone penetrating pin, said shank provided with a bone penetrating element at a first end and said removal facilitating means at a second end; said cap means detachably mounted on said driving head.

3. The combination as defined in claim 2 wherein said removal facilitating means comprises a driving head with a substantially square cross-section.

4. The combination as defined in claim 3 wherein said driving head is provided with a slot extending from one side to the other of said head.

5. The combination as defined in claim 2 wherein said torque transferring means comprises upper and lower cylindrical portions depending from said torque applying means, said cylindrical portions having first and second diameters, respectively, connected by said torque limiting means.

6. The combination as defined in claim 5 wherein said torque limiting means comprises an intermediate cylindrical portion having a diameter substantially smaller than either of said first and second diameters, wherein said intermediate portion is constructed to fail in shear upon the application of torque greater than a predetermined maximum.

7. The combination as defined in claim 1 wherein said torque applying means includes at least a pair of radially offset finger engageable arms extending outwardly in substantially opposite directions from an upper portion of said cap.

8. The combination as defined in claim 6 wherein said torque applying means includes at least a pair of radially offset finger engageable arms extending outwardly in substantially opposite directions from said upper portion of said cap.

9. The combination as defined in claim 6 wherein said lower portion of said cap is formed with an opening having a polygonal cross-section extending upwardly through substantially the entire lower portion of said cap, and adapted to receive said driving head of said shank, and wherein said torque applying means includes at least a pair of radially offset finger engageable arms extending outwardly in substantially opposite directions from a center portion of said cap.

10. The combination as defined in claim 2 wherein said bone penetrating element is comprised of a first material, and said shank and said removal facilitating means are comprised of a second material.

11. The combination as defined in claim 10 wherein said bone penetrating elements comprise titanium.

12. The combination as defined in claim 10 wherein said bone penetrating element comprises a single crystal alumina ceramic material.

13. The combination as defined in claim 1 wherein said bone penetrating pin is a skull pin and said shank is threaded along substantially its entire length with the exception of said removal facilitating means.

14. The combination as defined in claim 1 wherein said elongated shaft is provided with a bone pin engaging tip at one end and a first socket at the other end, said cap means slidably mounted on said elongated shaft, and wherein said cap means is formed with a second socket in substantial vertical alignment with said first socket; and wherein said means for transferring torque to said elongated shaft including torque limiting means comprises an insert member designed to fail at a selected torque level.

15. The combination as defined in claim 14 wherein said bone pin engaging tip comprises a tool head adapted to be received in said bone pin.

16. The combination as defined in claim 14, wherein said insert member comprises an upper portion and a lower portion separated by a peripheral, annular groove, and wherein said insert means fails in shear in the area of said groove.

17. The combination as defined in claim 16 and further including a plurality of interchangeable insert members, designed to fail at selected maximum torque levels.

18. The combination as defined in claim 17 wherein said interchangeable insert members are coded to indicate torque failure levels.

19. The combination as defined in claim 16 wherein said upper and lower portions of said insert member and said first and second socket members have complimentary polygonal cross-sectional shapes.

20. The combination as defined in claim 14 wherein said torque applying means comprises a handle extending radially outwardly from an upper portion of said cap means, said second socket formed in said upper portion of said cap means and opening downwardly, away from said handle, said cap means further provided with a retention sleeve for slidably mounting the cap means with respect to said shaft and wherein said second socket and said retention sleeve are axially-spaced from one another and in substantial axial alignment.

21. The combination as defined in claim 20 wherein said cap means and said elongated shaft are arranged such that said first socket provided at the other end of said elongated shaft is captured between said second socket and said retention sleeve.

22. A skull pin and removable cap comprising:
an externally threaded shank having a first skull engaging end and a second driving end, said threaded shank and said skull engaging end formed of different materials, said driving end receiving said removable cap provided with torque applying and torque limiting means, and wherein said driving end is further provided with means for receiving a tool by which said skull pin may be removed in the event of failure of said torque limiting means.

23. A skull pin as defined in claim 22 wherein said removable cap comprises upper and lower cylindrical portions of substantially equal diameters and wherein said torque limiting means comprises an intermediate portion of relatively smaller diameter connecting said upper and lower portions, said intermediate portion designed for failure upon application of torque beyond a predetermined maximum.

24. A skull pin as defined in claim 23 wherein said predetermined maximum is about seven inch pounds.

25. A skull pin as defined in claim 22 wherein said torque applying means includes arms extending in opposite directions from said upper portion of said cap.

26. A skull pin as defined in claim 23 wherein said lower cylindrical portion is formed with aperture defining means for mating engagement with said driving end.

27. In combination with a halo crown for immobilizing a patient's skull during medical treatment or operative procedure, wherein said halo crown comprises a generally ring-shaped rigid member having interior cross-dimensions larger than the diameter of the patient's head, and means defining a plurality of threaded openings extending through said generally ring-shaped rigid member, a plurality of skull pins adjustably received in said openings to adjust the extent of penetration of each of said skull pins into an interior volume defined by said generally ring-shaped rigid member, wherein each of said skull pins comprises an exteriorly threaded elongated shank having first and second ends, a skull engaging portion rigidly connected to one of said shank ends and terminating in a pointed tip, and a removable cap engageable with the other of said shank ends, said cap comprising both torque application and torque limiting means, said other of said shank ends provided with tool engaging means for permitting removal of said in in the event of failure of said torque limiting means.

28. The combination as defined in claim 27 wherein said removable cap comprises upper and lower cylindrical portions of substantially equal diameters and wherein said torque limiting means comprises an intermediate portion of relatively smaller diameter and interconnecting said upper and lower portions, said intermediate portion designed for failure upon application of torque beyond a predetermined maximum.

29. The combination as defined in claim 28 wherein said predetermined maximum is about seven inch pounds.

30. The combination as defined in claim 28 wherein said torque applying means includes oppositely extending arms integrally formed on said upper portion of said cap.

* * * * *